United States Patent [19]

Binns et al.

[11] 4,198,244
[45] Apr. 15, 1980

[54] FLUORESCING AGENTS FOR DENTAL PORCELAIN

[75] Inventors: David B. Binns, Barlaston; Ian K. Bloor, Audlem, both of England

[73] Assignee: National Research Development Corporation, London, England

[21] Appl. No.: 894,481

[22] Filed: Apr. 7, 1978

[51] Int. Cl.² .......................... C09K 3/00; C09K 11/46
[52] U.S. Cl. .......................................... 106/35; 106/45; 252/301.4 R; 252/301.6 R
[58] Field of Search ................................. 106/35, 45; 252/301.4 R, 301.6 R; 250/462–468

[56] References Cited

U.S. PATENT DOCUMENTS

| 2,406,208 | 8/1946 | Erdle | 106/45 |
| 2,895,050 | 7/1959 | Lee et al. | 250/71 |
| 4,026,816 | 5/1977 | Ranby et al. | 252/301.4 R |

OTHER PUBLICATIONS

Journal of Dental Research, IADR Abstracts, #500, 1976, Wozniak et al.

Primary Examiner—Theodore Morris
Attorney, Agent, or Firm—Finnegan, Henderson, Farabow, Garrett & Dunner

[57] ABSTRACT

A dental porcelain composition which includes, as fluorescing agents,
  0.05 to 2% by weight of $CeO_2$ and
  0.1 to 0.5% by weight of $Tb_2O_3$.

12 Claims, No Drawings

FLUORESCING AGENTS FOR DENTAL PORCELAIN

This invention relates to dental porcelain compositions and in particular to dental porcelain compositions containing fluorescing agents.

Natural human teeth fluoresce when exposed to ultraviolet radiation emitting light which generally varies from bluish-white to yellowish-white. Conventional dental porcelain compositions do not emit in this region when exposed to ultraviolet radiation and therefore to simulate the fluorescence of natural teeth fluorescing agents based on uranium have been added to the dental porcelain compositions. The use of uranium in this way is a radiological hazard and it is desirable that its use be discontinued.

It has been found that the colour emitted from natural teeth when exposed to ultraviolet radiation varies from tooth to tooth and within individual teeth. The colours are normally in the region bluish-white to yellowish-white but individual teeth vary considerably within this region. Thus the target colour for the fluorescence of dental porcelain is to a certain extent a matter of taste and desirable colours will occupy an appreciable area of colour space when plotted, for example on the CIE Chromaticity Diagram.

The invention has been made with the above points in mind.

According to the present invention there is provided a dental porcelain composition which includes, as fluorescing agents,
0.05 to 2% by weight of $CeO_2$ and
0.1 to 0.5% by weight of $Tb_2O_3$.

It has been found that the inclusion of 0.05 to 2% by weight cerium oxide and 0.1 to 0.5% by weight terbium oxide in conventional dental porcelain compositions allows the fluorescence of natural teeth to be simulated. Compositions containing these fluorescing agents are non-radioactive. With increasing $Tb_2O_3$ content the fluorescent emission changes from bluish-white to greenish-yellow and thus the general colour range emitted by natural teeth may be simulated. For example, 0.1% by weight $CeO_2$ and 0.25% by weight $Tb_2O_3$ will provide a substantially neutral white fluorescence when exposed to ultraviolet radiation.

The colour of the fluorescent emission may be modified as desired by the addition of trace amounts of one or more of the following oxides:

| | |
|---|---|
| $Dy_2O_3$ | up to 0.2% by weight to produce yellow tones, |
| $V_2O_5$ | up to 0.1% by weight to produce yellow tones, |
| $Sm_2O_3$ | up to 0.2% by weight to produce pink tones, and |
| $Eu_2O_3$ | up to 0.2% by weight to produce pink tones. |

The ranges for the oxides used as fluorescing agents in the dental porcelain compositions of the invention are critical in order to simulate the fluorescent emission of natural teeth. While in principle it is possible to combine emissions of different colours to produce white fluorescence in practice it is not possible to predict with any degree of certainty the fluorescent colour of any particular combination of oxides owing to interaction between the constituent oxides. The colour emitted by each of the oxides used in the invention when illuminated by mercury discharge lamp with a Wood's glass filter, the light of which is in the region 300 to 400 nm is as follows:

| | |
|---|---|
| $CeO_2$ | blue |
| $Tb_2O_3$ | green |
| $Dy_2O_3$ | yellow |
| $V_2O_5$ | yellow |
| $Sm_2O_3$ | orange |
| $Eu_2O_3$ | orange-red. |

We have found that if the cerium oxide content of the dental porcelain is increased above 2% by weight the emission falls rapidly owing to a self quenching effect. If the terbium oxide content is increased above 0.5% the fluorescent emission becomes unacceptable for simulating natural teeth as the colour changes to green tones. The other oxides must be used within the stated ranges in order to achieve a fluuorescence simulating that of natural teeth.

The fluorescing agents used in the invention must be thoroughly dispersed in the dental porcelain. Typical dental porcelains including both dentine and enamel porcelains have a formulation within the ranges in the following Table 1.

TABLE 1

| oxide | Porcelains for jacket crowns % | Porcelains for metal-bonded restorations % |
|---|---|---|
| $SiO_2$ | 60–70 | 55–70 |
| $Al_2O_3$ | 8–20 | 14–20 |
| CaO | 0–4 | 0–2 |
| $Na_2O$ | 2–5 | 4–8 |
| $K_2O$ | 6–9 | 9–14 |
| $B_2O_3$ | 5–10 | 0–4 |

The above porcelain compositions are low firing porcelains having a firing temperature in the range 900° to 950° C.

A specific example of a formulation which was tested is

| Oxide | Weight % |
|---|---|
| $SiO_2$ | 65.9 |
| $Al_2O_3$ | 13.2 |
| CaO | 1.8 |
| $K_2O$ | 7.6 |
| $B_2O_3$ | 7.3 |
| $Na_2O_3$ | 4.1 |

The fluorescing agents may be added to a pre-prepared porcelain by melting the porcelain and dispersing the fluorescing agents in the melt or by mixing the fluorescing agents with the constituents of the porcelain prior to melting.

When the fluorescing agents are added to a melted porcelain it is preferable that the porcelain is heated to at least 1200° C., more preferably 1400° C. It has been found that the intensity of emission increases with increased melting temperature. It is believed that this result is due to a more thorough distribution of fluorescing agents which is achieved at the high melting temperatures when the viscosity of the melt is lower.

The most effective method is to disperse the fluorescent oxides with the constituents of porcelain composition prior to the original melting or during the original melt which may be at temperatures over 1500° C.

The invention will now be illustrated by the following Examples in which all parts and percentages are by weight.

Various porcelain compositions were prepared and examined under ultraviolet light. The compositions and results are presented in Table 2.

TABLE 2

| | Composition | | | | Fluorescent (1) colour cast |
|---|---|---|---|---|---|
| | Base porcelain | $CeO_2$ % | $Tb_2O_3$ % | $Dy_2O_3$ | $Sm_2O_3$ | |
| 1 | 100 | 0.1 | 0.2 | — | — | Blue |
| 2 | 100 | 0.1 | 0.25 | — | — | Neutral |
| 3 | 100 | 0.1 | 0.30 | — | — | Yellow |
| 4 | 100 | 0.1 | 0.2 | 0.10 | — | Yellow-pink |
| 5 | 100 | 0.1 | 0.2 | — | 0.05 | Pink |

(1) All the porcelain colours are close to neutral white having slight tones of the colours indicated all of which would be useful in matching natural tooth fluorescence.

We claim:

1. A dental porcelain composition, comprising dental procelain and, as fluorescing agents, from 0.05 to 2% by weight $CeO_2$ and from 0.1 to 0.5% by weight of $Tb_2O_3$ based on the weight of the procelain.

2. The porcelain composition of claim 1 which includes about 0.1% $CeO_2$ and about 0.25% $Tb_2O_3$.

3. A dental porcelain composition as claimed in claim 1 or 2 which additionally includes one or more of the fluorescent oxides:

| | |
|---|---|
| $Dy_2O_3$ | in an amount up to 0.1% by weight, |
| $V_2O_5$ | in an amount up to 0.1% by weight, |
| $Sm_2O_3$ | in an amount up to 0.2% by weight and |
| $Eu_2O_3$ | in an amount up to 0.2% by weight. |

4. A method for preparing a dental porcelain composition which fluoresces under ultraviolet radiation comprising melting a dental porcelain at a temperature of at least 1200° C., adding to the resulting melt and thoroughly disbursing therein from 0.05 to 2% by weight of $CeO_2$ and from 0.1 to 0.5% by weight $Tb_2O_3$ based on the weight of the procelain and thereafter allowing the melt to cool.

5. The method of claim 4 in which the dental porcelain is melted at 1400° C.

6. A method for preparing a dental porcelain composition which fluoresces under ultraviolet light comprising melting a dental porcelain at a temperature of at least 1200° C., mixing with the porcelain prior to melting or during melting from 0.05 to 2% by weight of $CeO_2$ and from 0.1 to 0.5% by weight $Tb_2O_3$ based on the weight of the porcelain and thereafter allowing the melt to cool.

7. The method of claim 6 in which the dental porcelain is melted at 1500° C.

8. A method as claimed in any one of claims 4, 5, 6 or 7 in which 0.1% by weight $CeO_2$ and 0.25% by weight $Tb_2O_3$ are used.

9. A method as claimed in any one of claims 4, 5, 6 or 7 in which one or more of the fluorescent oxides:

| | |
|---|---|
| $Dy_2O_3$ | in an amount up to 0.1% by weight, |
| $V_2O_5$ | in an amount up to 0.1% by weight, |
| $Sm_2O_3$ | in an amount up to 0.2% by weight, and |
| $Eu_2O_3$ | in an amount up to 0.2% by weight | are additionally used.

10. A dental porcelain when prepared by a method as claimed in any one of claims 4, 5, 6 or 7.

11. The dental porcelain of claim 10, in which 0.1% by weight $CeO_2$ and 0.25% by weight $Tb_2O_3$ are used.

12. The dental porcelain of claim 10, in which one or more of the fluorescent oxides:

| | |
|---|---|
| $Dy_2O_3$ | in an amount up to 0.1% by weight, |
| $V_2O_5$ | in an amount up to 0.1% by weight, |
| $Sm_2O_3$ | in an amount up to 0.2% by weight, and |
| $Eu_2O_3$ | in an amount up to 0.2% by weight | are additionally used.

* * * * *